(12) United States Patent
Hertlein (10) Patent No.: US 9,883,718 B2
(45) Date of Patent: Feb. 6, 2018

(54) METHOD FOR MANUFACTURING FASTENERS AND PRECURSOR WEBS, A FASTENER AND A PRECURSOR WEB

(71) Applicant: 3M INNOVATIVE PROPERTIES COMPANY, St. Paul, MN (US)

(72) Inventor: Thomas Hertlein, Neuss (DE)

(73) Assignee: 3M Innovative Properties Company, St. Paul, MN (US)

( * ) Notice: Subject to any disclaimer, the term of this patent is extended or adjusted under 35 U.S.C. 154(b) by 352 days.

(21) Appl. No.: 14/410,462

(22) PCT Filed: Jun. 24, 2013

(86) PCT No.: PCT/US2013/047326
§ 371 (c)(1),
(2) Date: Dec. 22, 2014

(87) PCT Pub. No.: WO2014/004379
PCT Pub. Date: Jan. 3, 2014

(65) Prior Publication Data
US 2015/0335105 A1    Nov. 26, 2015

(30) Foreign Application Priority Data

Jun. 26, 2012   (EP) .................................. 12173686

(51) Int. Cl.
*A44B 18/00*   (2006.01)
*A61F 13/62*   (2006.01)
*A61F 13/15*   (2006.01)

(52) U.S. Cl.
CPC ...... *A44B 18/0049* (2013.01); *A44B 18/0065* (2013.01); *A61F 13/15756* (2013.01);
(Continued)

(58) Field of Classification Search
CPC ............ A44B 18/0061; A44B 18/0065; A44B 18/0042; A44B 18/0049; Y10T 24/2792;
(Continued)

(56) References Cited

U.S. PATENT DOCUMENTS 3,426,400 A    2/1969    Lauro
3,536,518 A   10/1970    Drelich
(Continued)

FOREIGN PATENT DOCUMENTS

CA         2013950       10/1990
DE       102005040029     3/2006
(Continued)

OTHER PUBLICATIONS

International Search report for PCT International Application No. PCT/US2013/047326, dated Oct. 14, 2013, 5 pages.

*Primary Examiner* — Jack W Lavinder
(74) *Attorney, Agent, or Firm* — Steven A. Bern; Ted K. Ringsred (57) ABSTRACT

The invention relates to a method for forming a fastener having fastener members (23, 63) wherein molten polymer material is deposited by a deposition device onto a contact release surface (7, 27, 32), thereby forming preform projections (20, 60), which contact the front surface (21) of a carrier (13, 62) with their terminal ends (22, 61) and bond to the carrier (13, 62). The carrier (13, 62) is removed with the preform projections (20, 60) attached, thereby separating the preform projections (20, 60) from the contact release surface (7, 27, 32) and forming fastening members (23, 63) projecting from the front surface (21) of the carrier (13, 62). The invention relates further to a method for manufacturing a precursor web (66) for manufacturing a fastener, a fastener web (91, 94,101) for engaging with a loop fabric and a precursor web (66) for manufacturing a fastener.

8 Claims, 7 Drawing Sheets

(52) U.S. Cl.
CPC ............. *A61F 13/625* (2013.01); *Y10T 24/27* (2015.01); *Y10T 24/2767* (2015.01)

(58) Field of Classification Search
CPC ....... Y10T 156/1089; Y10T 428/24017; Y10T 24/2767; Y10T 24/27; A61F 13/15756; A61F 13/625
See application file for complete search history.

(56) References Cited

U.S. PATENT DOCUMENTS

| | | |
|---|---|---|
| 3,550,223 A | 12/1970 | Erb |
| 3,562,044 A | 2/1971 | Erb |
| 3,594,863 A | 7/1971 | Erb |
| 3,594,865 A | 7/1971 | Erb |
| 3,629,032 A | 12/1971 | Erb |
| 3,708,382 A | 1/1973 | Erb |
| 3,708,833 A | 1/1973 | Ribich |
| 4,056,593 A | 11/1977 | De Navas Albareda |
| 4,169,303 A | 10/1979 | Lemelson |
| 4,198,734 A | 4/1980 | Brumlik |
| 4,215,257 A | 7/1980 | Repplinger |
| 4,307,493 A | 12/1981 | Ochiai |
| 4,330,907 A | 5/1982 | Ochiai |
| 4,338,800 A | 7/1982 | Matsuda |
| 4,454,183 A | 6/1984 | Wollman |
| 4,462,784 A | 7/1984 | Russell |
| 4,532,157 A | 7/1985 | Schmidt |
| 4,562,099 A | 12/1985 | Hinchcliffe |
| 4,587,152 A | 5/1986 | Gleichenhagen |
| 4,672,893 A | 6/1987 | Mammarella |
| 4,725,221 A | 2/1988 | Blanz |
| 4,846,815 A | 7/1989 | Scripps |
| 4,876,982 A | 10/1989 | Claassen |
| 4,938,835 A | 7/1990 | Ludwig |
| 4,984,339 A | 1/1991 | Provost |
| 5,013,498 A | 5/1991 | Froeschke |
| 5,040,275 A | 7/1991 | Eckhardt |
| 5,058,247 A | 10/1991 | Thomas |
| 5,116,563 A | 5/1992 | Thomas |
| 5,122,219 A | 6/1992 | Ludwig |
| 5,180,534 A | 1/1993 | Thomas |
| 5,230,851 A | 7/1993 | Thomas |
| 5,318,741 A | 6/1994 | Thomas |
| 5,325,569 A | 7/1994 | Goulait |
| 5,326,415 A | 7/1994 | Thomas |
| 5,385,706 A | 1/1995 | Thomas |
| 5,392,498 A | 2/1995 | Goulait |
| 5,520,676 A | 5/1996 | Lavash |
| 5,540,673 A | 7/1996 | Thomas |
| 5,586,371 A | 12/1996 | Thomas |
| 5,622,578 A | 4/1997 | Thomas |
| 5,628,952 A | 5/1997 | Holmes |
| 5,664,302 A | 9/1997 | Thomas |
| 5,679,302 A | 10/1997 | Miller |
| 5,720,740 A | 2/1998 | Thomas |
| 5,868,987 A | 2/1999 | Kampfer |
| 5,879,604 A | 3/1999 | Melbye |
| 6,132,660 A | 10/2000 | Kampfer |
| 6,248,276 B1 | 6/2001 | Parellada |
| 6,266,871 B1 | 7/2001 | Edwards |
| 6,503,855 B1 | 1/2003 | Menzies |
| 6,592,800 B1 | 7/2003 | Levitt |
| 6,623,469 B1 | 9/2003 | Thomas |
| 6,708,378 B2 | 3/2004 | Parellada |
| 6,838,154 B1 | 1/2005 | Varona et al. |
| 8,388,880 B2 | 3/2013 | Tuma |
| 2001/0016245 A1 | 7/2001 | Tuman |
| 2002/0116799 A1 | 7/2002 | Martin |
| 2003/0084996 A1 | 5/2003 | Alberg |
| 2003/0085485 A1 | 5/2003 | Seidel |
| 2003/0104746 A1 | 6/2003 | Menzies |
| 2004/0031130 A1 | 2/2004 | Clarner |
| 2004/0060097 A1 | 4/2004 | Bamber |
| 2004/0102745 A1 | 5/2004 | Linker, III |
| 2004/0178544 A1 | 9/2004 | Jackson |
| 2005/0081342 A1 | 4/2005 | Erickson |
| 2005/0081344 A1 | 4/2005 | Clarner |
| 2005/0081346 A1 | 4/2005 | Clarner |
| 2006/0090307 A1 | 5/2006 | McDaniel |
| 2007/0137007 A1 | 6/2007 | Martin |
| 2008/0017836 A1 | 1/2008 | Saito |
| 2008/0038507 A1 | 2/2008 | Seth |
| 2008/0060173 A1 | 3/2008 | Zhang |
| 2008/0178436 A1 | 7/2008 | Zhang |
| 2009/0065967 A1 | 3/2009 | Clune |

FOREIGN PATENT DOCUMENTS

| | | |
|---|---|---|
| EP | 0265155 | 4/1988 |
| EP | 0276970 | 8/1988 |
| EP | 0297070 | 12/1988 |
| EP | 0319249 | 6/1989 |
| EP | 0321232 | 6/1989 |
| EP | 0324577 | 7/1989 |
| EP | 0325473 | 7/1989 |
| EP | 0333031 | 9/1989 |
| EP | 0353972 | 2/1990 |
| EP | 0381087 | 8/1990 |
| EP | 0388681 | 9/1990 |
| EP | 0429249 | 5/1991 |
| EP | 0464753 | 1/1992 |
| EP | 0476992 | 3/1992 |
| EP | 0580073 | 1/1994 |
| EP | 0603189 | 6/1994 |
| EP | 0660677 | 7/1995 |
| EP | 0692940 | 1/1996 |
| EP | 0692941 | 1/1996 |
| EP | 0778688 | 6/1997 |
| EP | 0798974 | 10/1997 |
| EP | 0929281 | 7/1999 |
| EP | 1262531 | 12/2002 |
| FR | 2432108 | 2/1980 |
| GB | 1193130 | 5/1970 |
| GB | 1300077 | 12/1972 |
| GB | 2188229 | 9/1987 |
| GB | 2233876 | 1/1991 |
| GB | 2242612 | 10/1991 |
| GB | 2279106 | 12/1994 |
| JP | 51002512 | 1/1976 |
| JP | 55137942 | 10/1980 |
| JP | H04058322 | 2/1992 |
| WO | WO 1987-06522 | 11/1987 |
| WO | WO 1992-00023 | 1/1992 |
| WO | WO 1992-10957 | 7/1992 |
| WO | WO 1992-20250 | 11/1992 |
| WO | WO 1993-00215 | 1/1993 |
| WO | WO 1993-03644 | 3/1993 |
| WO | WO 1994-04053 | 3/1994 |
| WO | WO 1994-09668 | 5/1994 |
| WO | WO 1994-13168 | 6/1994 |
| WO | WO 1994-22338 | 10/1994 |
| WO | WO 1994-22339 | 10/1994 |
| WO | WO 1994-027461 | 12/1994 |
| WO | WO 1994-29070 | 12/1994 |
| WO | WO 1996-13996 | 5/1996 |
| WO | WO 1996-20613 | 7/1996 |
| WO | WO 1996-25905 | 8/1996 |
| WO | WO 1997-05792 | 2/1997 |
| WO | WO 1998-10728 | 3/1998 |
| WO | WO 1998-29003 | 7/1998 |
| WO | WO 1999-06623 | 2/1999 |
| WO | WO 2000-000053 | 1/2000 |
| WO | WO 2000-020200 | 4/2000 |
| WO | WO 2000-060974 | 10/2000 |
| WO | WO 2001-033989 | 5/2001 |
| WO | WO 2001-067911 | 9/2001 |
| WO | WO 2002-013740 | 2/2002 |
| WO | WO 2002-013741 | 2/2002 |
| WO | WO 2002-013742 | 2/2002 |
| WO | WO 2002-013743 | 2/2002 |
| WO | WO 2002-013744 | 2/2002 |
| WO | WO 2002-013746 | 2/2002 |
| WO | WO 2002-013747 | 2/2002 |

(56) References Cited

FOREIGN PATENT DOCUMENTS

| | | |
|---|---|---|
| WO | WO 2002-013748 | 2/2002 |
| WO | WO 2002-013749 | 2/2002 |
| WO | WO 2002-069864 | 9/2002 |
| WO | WO 2003-000483 | 1/2003 |
| WO | WO 2005/067756 | 7/2005 |
| WO | WO 2006-099000 | 9/2006 |
| WO | WO 2006-0108049 | 10/2006 |
| WO | WO 2008-033529 | 3/2008 |
| WO | WO 2008-033629 | 3/2008 |
| WO | WO 2008-033816 | 3/2008 |
| WO | WO 2008-125253 | 10/2008 |

METHOD FOR MANUFACTURING FASTENERS AND PRECURSOR WEBS, A FASTENER AND A PRECURSOR WEB

CROSS REFERENCE TO RELATED APPLICATIONS

This application is a national stage filing under 35 U.S.C. 371 of PCT/US2013/047326, filed Jun 24, 2013, which claims priority to European Application No. 12173686.2, filed Jun 26, 2012, the disclosure of which is incorporated by reference in its/their entirety herein.

DESCRIPTION

The present invention relates to a method for manufacturing a fastener having fastening members, particularly a male fastener for a hook and loop fastening system, a method for manufacturing a precursor web for manufacturing said fastener, a fastener web for engaging with a loop fabric wherein the fastener web comprises a multiplicity of said fastening members and a precursor web suitable for manufacturing said fastener.

It is common to use certain types of hook-and-loop type mechanical fasteners for fixing disposable diapers, training pants and incontinence garments around a wearer. One approach is a thin, male component as a fastener for engagement with low loft loop materials, preferable nonwoven fabrics as the female component. The word "loop", as used in this document, also includes essentially flat lying, free sections of filaments, such as those of a thin nonwoven or knit fabric, capable of mechanically engaging with a male fastener component, the usage of the word being in accordance with its current general use in the art of reclosable fasteners.

The male component generally comprises a carrier having a front surface, onto which a plurality of fastening members for engagement with the loops of the female component are distributed. When the male component and the female component are pressed together in a face to face relationship to close the fastening device, the loops entangle the fastening members such that the components will not easily disengage. For opening the fastener a gradual peeling force is applied such that the fastening members release or break the loops. In any case, male and female components have enough integrity to be fastened multiple times.

For manufacturing a male fastener, it is known to integrally form a carrier provided with the fastening members by introducing thermoplastic resin from an extruder into a nip formed between two rolls. One of these rolls has cavities for forming the fastening members (US 2004/0031130 A1).

Another method for manufacturing a male fastener is disclosed in U.S. Pat. Nos. 5,326,415 and 5,392,498. In this method, a flexible carrier is fed through the nip between two rolls. One of these rolls is embodied as a rotary screen print cylinder, whereby molten material is deposited onto the carrier while running through the nip thereby forming the fastening members onto the front surface of the carrier in a desired pattern.

It is also known to deposit molten polymeric material provided by an extruder onto a carrier web, which is then fed around the mantle surface of a tool roll with the front surface of the carrier being in contact with the tool roll. The tool roll has a plurality of cavities forming the polymeric material to stem like fastening members (US 2001/0016245 A1).

Moreover, U.S. Pat. Nos. 5,679,302 and 5,879,604 discloses a method for manufacturing a male fastener also using an extruder, which deposits thermoplastic resin heated to a molten status onto the mantle surface of a roll having a plurality of cavities. The thermoplastic resin is stripped off the roll by a stripper roll thereby forming a carrier having fastening members.

In the foregoing two documents, it is described to feed the carrier provided with the fastening members through a gap between two calendar rolls. One of these rolls contact predetermined portions of the distal ends of the fastening members, thereby heating the tips of the fastening members to a temperature at which they will readily deform under mechanical pressure, forming these tips into generally uniform disc shaped mushroom heads. A similar method for forming the tips of fastening members is disclosed in U.S. Pat. Nos. 6,592,800 B1, 6,248,276 B1 and 6,708,378 B2.

In WO 01/33989 A1, particles are randomly scattered onto the front surface of a carrier supported by an endless conveyor belt using a scatter head of a scatter coater. The conveyor belt is heated by heat radiators melting the carrier and the particles dispersed onto the carrier. Thereafter, a cooling unit solidifies the carrier and the particles thus fixing the particles to the front surface of the carrier.

Another method for a manufacturing male fastener is disclosed in WO 2006/099000 A2, WO 2008/033629 A2 and US 2008/0178436 A1. The method is carried out in an apparatus having a substrate web with a contact release surface embodied as a conveyor belt running around two rolls. Polymer particles are dispersed onto the horizontal contact release surface of the substrate web by using a scatter unit. The underside of the substrate web is heated by a heating device, thereby softening or melting the particles and forming them to preform projections having acute contact angles. Then, the contact release surface is cooled down by an air blower, thereby solidifying the preform projections. A carrier is laid over the preform projections contacting their terminal ends. The carrier is heated by a hot air blowing unit on its back surface enough for softening the carrier and fixing it with the terminal ends of the preform projections. The terminal ends of the preform projections are also melted from the heat to a suitable extent for fusing them to the carrier. Thereafter, the carrier is cooled by an air blower. The carrier together with the fastening members bonded thereto is separated and removed from the contact release surface and then wound up in a reel. The so formed fastening members have tops with a rim overhanging the base and bordered all around by an edge.

The disadvantage of this method is that the distribution of the fastening members is irregular and that at least two heating devices are necessary for softening the particles dispersed onto the contact release surface and for melting the carrier and the preform projections in order to bond them together. Beside the heating devices, at least two cooling devices are necessary to bond the preform projections with the contact release surface and to solidify the heated carrier and the fastening members. Particularly the heating devices consume a lot of energy. Moreover, it is inevitable that the preform projections obtain a spherical surface resulting in cup like fastening members with a convex mantle surface and a flat top surface at their terminal ends.

It is therefore an object of the present invention to provide a method for manufacturing a fastener, particularly a male fastener for a hook and loop fastening system, which is more economical and which enables one to obtain fastening members having a desired cap shape and defined position, allowing better control over the engagement with female components. It is a further object of the present invention to provide a fastener better suited for engaging with a female component. Moreover, it is an object of the invention to provide a method for manufacturing a precursor web suited for manufacturing a fastener and to provide an according precursor web.

With respect to the method for manufacturing a fastener, the invention generally comprises the steps of:
- providing a carrier with a front surface;
- providing a contact release surface;
- providing a deposition device having a plurality of cavities;
- providing a polymer material heated to a molten status;
- filling said molten polymer material into said cavities;
- depositing said molten polymer material from said cavities onto said contact release surface having a temperature below the softening or melting temperature of said molten polymer material, thereby forming preferable discrete preform projections sitting on and projecting from the contact release surface to their corresponding terminal ends;
- said preform projections being in contact with the contact release surface for a time sufficient to solidify next to the contact release surface;
- contacting the front surface of the carrier with the terminal ends of said preform projections and bonding them to the carrier;
- removing the carrier with the preform projections attached, thereby separating the preform projections from the contact release surface; and
- thereby forming fastening members projecting from the front surface of the carrier.

Different to the method disclosed for example in WO 2006/099000 A2, the present invention uses a deposition device having a plurality of cavities enabling the molten polymer material to be deposited in a desired, well defined pattern and shape onto the contact release surface. Contrary to this the polymer particles are deposited in the method of WO '000 in a random manner on the contact release surface. Moreover, in the present invention discrete fastening members can be realized which have no direct convection with each other.

The general idea of this invention can be realized into two alternative methods. In the first alternative embodiment of such methods, the terminal ends of the preform projections are still molten or semi-molten, when they come into contact with the front surface of the carrier. It is not necessary to apply additional heat to the preform projections if the time between the deposition of the molten polymer material onto the contact release surface and the contact with the front surface of the carrier is short enough to maintain the terminal ends of the preform projections still molten or semi-molten. So, this special method works very economically. Also, this first alternative has the advantage that the preform projections can be formed onto the substrate in a desired pattern. The preform projections generally have an inverted cup shape which is characterized by a convex mantle surface wherein the diameter of the terminal end of the perform projection (i.e. the exposed terminal end of the preform projection when being still attached to the contact release surface) is smaller than the diameter of the opposed surface of said preform projection attached to the contact release surface. Likewise the fastening members obtained from said preform projections in said first method exhibit a mantle surface wherein the diameter of the terminal end of the fastening member (i.e. the exposed terminal end of fastening means attached to the carrier) is larger than the diameter of the opposed surface of said fastening member that is attached to the carrier. Above and below the term convex mantle shape denotes a mantle shape that is outwardly curved relative to a straight mantle surface. Correspondingly a concave mantle surface is defined above and below as being inwardly curved relative to a straight mantle surface. Both the preform projections and the fastening members obtained in the first method preferably exhibit a convex mantle shape. It was found that preform projections having a convex mantle shape generally engage effectively with the loops of a female component.

In a second alternative embodiment of the method according to claim 1, the preform projections will be kept in contact with the contact release surface for a time sufficient to solidify completely and then at least the terminal ends of the preform projections are re-melted to a semi-molten or molten status before and/or while contacting them with the front surface of the carrier. Preferable, the terminal ends should be heated in an apparatus region, where the front surface of the carrier is coming into contact with said terminal ends. This method allows the preform projections to solidify so that re-melting of at least the terminal ends of the preform projections to a semi-molten or molten status is necessary. This provides a more reliable process so that bonding to the carrier is independent of parameters like speed of the substrate with the preform projections, cooling temperature as well as type and temperature of the polymer material. Apart from that, the method of this alternative allows to control the shape of the preform projections because the complete solidification of the perform projections allows to at least partly maintain their initial shape as defined by the shape of the cavities of the deposition device if desired. As is exemplified below this method allows, for example, to provide fastening members having mantle surfaces with a convex, essentially straight and/or concave shape, respectively. In addition, the preform projections on the release surface can be wound up for later heating and transfer to a carrier at a different time and/or place.

In order to enhance the bonding between the fastening members and the carrier, particularly if the carrier has a smooth front surface as is the case if the carrier is embodied as a film or foil, it is suggested that the front surface of the carrier is heated at least to its softening temperature in the region, where the preform projection comes into contact with the carrier. Heating of the front surface of the carrier can simultaneously be used to re-melt at least the terminal ends of the preform projections if they have been cooled beforehand to a temperature being lower than their softening or melting temperature. Alternatively, the heat energy of the terminal ends of the preform projections may be used to heat the front surface of the carrier sufficiently to provide bonding of the preform projections to the carrier. Furthermore, a welding unit may be used to heat the front surface of the carrier sufficiently to provide bonding of the preform projections to the carrier.

Since the contact release surface is heated by the heat of the molten polymer material deposited thereon, cooling of the base of the preform projections next to the contact release surface can be accelerated, if the contact release surface is actively cooled by a cooling device, for example a cooled plate or roll, over which the substrate is fed, or by a cooling blower. If the cooling effect of the cooling device is controllable, the temperature of the substrate can be kept on a constant temperature so that the method is more reliable.

The method of the present invention is not limited to the use of a specific material for the carrier. In the most simple execution, the carrier can be a flat polymer film, such that the resulting fastener is processed and applied in a similar way as known fasteners e.g. disclosed in U.S. Pat. No. 5,679,302 or US 2004/0031130 A1. That means the fastener is slit and wound into rolls. For application, the roll is unwound and e.g. patches are cut and bonded to the desired spot of e.g. a hygiene article. However a preferred execution of the invention is to have a carrier that is not only the hook backing but also provides an additional function in the e.g. hygiene article, including carriers like a multi-layer polymer film, a woven or knitted fabric, a multi-layer fabric, a non-woven or combination thereof. Moreover, printed or unprinted webs, breathable or non-breathable webs, films, paper and further elastic webs.

The carrier can consist of two or more superposed layers. In that case, bonding the preform projections to the front surface of the carrier can also provide bonding of the superposed layers in the areas of the fastening members. For example, the layers are heated to a temperature such that their opposing surfaces are bonded, for example by a welding unit. This welding unit can be located where the layers are fed together and the so formed carrier comes into contact with the preform projections. An example is the lamination of a non-woven with a film to form a non-woven back sheet with fastening members. When sonic welding is used, the heat will only be generated at the stems of the hooks. In case of the back sheet, during the bonding process the hook resin strikes through the non-woven and bonds to the film. In case of similar materials, the sonic welding could melt the layers and bond all together. Such a process saves the use of adhesive for bonding the non-woven to the backsheet film.

Preferably, a first polymer material is used for forming the preform projections and at least the front surface of the carrier is formed of a second material different in at least one property than the first material. The polymer material for forming the preform projections can be polyester-based. Also hot-melt construction adhesives could provide a good bond to different surfaces and still would have sufficient strength after cooling. Wax of PP or other polyolefins or blends of polyolefins can also be used. It is possible to mix an additive into the resin to provide better optical appearance by adding colour batch or agents that effect haze and gloss. The colour batch can be an optical brightener that allows detection of the transferred fastening members. Other additives can be mixed in to improve product or processing properties. In order to enhance the bond of the fastening members to the carrier, coupling agents can be added. Fillers or additives that change flow properties can be used to adjust stringing of the polymer material and as such affect the height of the preform projections.

As already detailed above, the preform projections are preferably formed such that the fastening members bonded onto the front surface of the carrier have an attached end area and have a top surface area at the terminal end, the attached end area of the fastening members preferably being smaller than the top surface area. The preform projections are preferably formed so that the fastening members exhibit a mantle surface extending between the terminal end and the attached end. The mantle surface preferably at least partially tapers between the terminal end and the attached end in the direction to the attached end. In particularly preferred embodiments the mantle surface of the fastening members has a convex, particularly lenticular or cup-type, essentially straight and/or concave shape. Moreover, it is possible in connection with the method of the present invention that the terminal ends of the fastening members bonded onto the front surface of the carrier are deformed, particularly by re-heating and then contacting them with a shaping surface of a shaping device, for example as disclosed in U.S. Pat. Nos. 5,679,302, 5,868,987, 6,132,660 and WO 2000/000, 053. So, further shapes of the terminal ends of the fastening members can be realized. However, in most cases it is sufficient to form the preform projections and hence the fastening members by choosing suitable cavities for depositing the molten polymer material onto the contact release surface.

The principle of the present invention can also be used for forming a precursor web, which is suitable for manufacturing fasteners. This method is characterized by the following steps:

providing a substrate web with a contact release surface;
providing a deposition device having a plurality of cavities;
providing a polymer material heated to a molten status;
filling said molten polymer material into said cavities;
depositing said molten polymer material from said cavities onto said contact release surface having a temperature below the softening or the melting temperature of said molten polymer material, thereby forming preferable discrete preform projections sitting on and projecting from the contact release surface to their corresponding terminal ends;
said preform projections being in contact with the contact release surface preferably for a time sufficient to solidify completely thereby forming a precursor web from which the preform projections are releasable;
removing the precursor web off the deposition device, particularly by winding up the precursor web onto a roll.

With the help of a deposition device having a plurality of cavities it is possible to form preform projections onto the substrate web in a desired shape and pattern. Moreover, discrete preform projections can be realized having no connections with each other by their material, but only via the carrier itself. The precursor web can be used to manufacture fasteners as suggested in claim 3 at a remote location, if that is desired. Also in this context, the term contact release surface means that the adherence of the preform projections to the contact release surface is lower than the adherence of preform projections to the carrier, so that the preform projections will transfer from the contact release surface to the carrier when the carrier is taken away. In any case, the bonding of the preform projections with the contact release surface is so low that the precursor web is not suited as a fastener.

The preform projections of the precursor web should be formed obtaining a mantle surface extending between the terminal end and the attached end whereby the mantle surface of the preform projections preferably at least partially tapers between the attached end and the terminal end in the direction of the terminal end. In particularly preferred embodiments, the mantle surface of the preform projections has a convex, particularly lenticular or cup-type, essentially straight and/or concave shape. This can be realized by using accordant shapes and/or, in particular, depths of the cavities of the deposition device and suitable polymer materials as disclosed, for example, in U.S. Pat. No. 5,325,569.

The contact release surfaces suited for the methods of this invention can be part of different means. In a first alternative, the means is embodied like a conveyor belt forming a closed loop that is moved around at least two rolls in the path of the deposition device as it is disclosed for example in WO 2006/099000 A2. A second alternative is that the contact release surface is formed by a rotating roll with its mantle surface next to the deposition device. A third alternative uses a substrate web of finite extension which is wound onto a roll, moved by uncoiling it from the roll and guided along the deposition device with the contact release surface of the substrate web next to the deposition device. The part that provides the contact release surface can be metal (e.g. belt or roller), thermo set (e.g. belt out of silicon rubber) or thermoplastic (e.g. film like substrate web). The contact release surface can be flat or have uniform or non-uniform structures. With respect to the polymer material used for forming the preform projections, the contact release surface can be treated for example to balance between good fixation of the preform projections prior to bonding and low release force to pull of the carrier with the transferred fasteners. In any case, the contact release surface should have a sufficient temperature resistance so that it is not impaired by the molten polymer material, or it should be actively cooled so that the temperature is maintained below a critical temperature for the substrate web.

For the methods in accordance with the invention, it is preferable to provide a deposition device embodied as a printing device having cavities on its surface such as, for example, a gravure printing roll having patterned cavities or having a rotary screen with holes as cavities. Above and below, the term cavities is used broadly and comprises both cavities and holes. The use of printing devices is preferred in the present invention because they allow to effectively control the shape of the preform projections and their positioning on the contact release surface. Such printing devices have the advantage that they are not expensive and are easy and quick to replace by another printing device in case of wear-off or to allow for forming different preform projections. The cavities can be of any shape, for example round, oval, hexagonal or star-like. One deposition device can have various cavity shapes to provide different properties in different areas of the carrier or precursor web. Moreover, various hole densities can be realized. The volume of the preform projections can be influenced by varying the cavity volume. The cavities can be arranged in a single or several macro patterns. The screen circumference can be a multiple of the length of the macro pattern. For example, if the carrier is used as backsheet in a pad for fixation to the underwear, the method would allow almost full coverage of the backsheet with fastening members without having projections in the edge area what might cause skin irritation or negatively affect the cut and seal process on the pad making line.

Beside the methods for manufacturing a fastener and a precursor web, the present invention provides a fastener web for engaging with a loop fabric comprising a carrier with a front surface, onto which a multiplicity of discrete polymeric fastening members is bonded preferably in a repeating pattern. The fastening members are formed out of a polymer material and have a terminal end with a top surface, an attached end and a mantle surface extending between the top surface and the attached end, wherein the mantle surface preferably at least partially tapers from the top surface to the attached end in the direction of the attached end. The term "discrete" means that the fastening members have no connection with each other by their polymeric material, but only via the carrier itself, while the term "repeating pattern" means that in any pattern the fastening members are similar with respect to the number, distribution and shapes resulting in similar and reproducible properties for each pattern. The term "the mantle surface of the fastening members at least partially tapers from the top surface of the terminal end to the attached end in the direction of the attached end" means that the mantle surface essentially continuously tapers in the direction of the attached end over at least part of its extension. The fastener web can be produced by the methods as disclosed above by using a deposition device for depositing the molten polymer material onto the contact release surface, the deposition device having a printing roll with cavities on its mantle surface or having a rotary screen with holes as cavities.

By using the method of the present invention, fastening members can be realized having mantle surfaces that preferably at least partially taper between the terminal end and the attached end in the direction of the attached end. In particularly preferred embodiments the mantle surface has a convex, particularly lenticular or cup-type, essentially straight and/or concave shape. Preferable, the top surface of the terminal of the fastening members are substantially flat and/or structured and/or have a shape that is substantially round, oval, hexagonal or star-like. As detailed above, the carrier can consist of two or more carrier layers bonded together at least at the attached ends of the fastening members. Moreover, it is possible that the fastening members in one pattern have different shapes and/or a different distribution so that the properties of the fastening members can be adapted to the meet particular requirements.

The present invention also relates to a precursor web for manufacturing a fastener, particularly a male fastener for a hook and loop fastener, comprising a substrate web with a contact release surface onto which a multiplicity of discrete preform projections of a polymer material is releasable bonded in a repeating pattern. These preform projections have a terminal end with a top surface, an attached end and a mantle surface extending between the top end and the attached end that preferably at least partially tapers from the attached end to the terminal end in the direction of the terminal end. The terms "discrete" and "repeating pattern" have the same meaning as detailed above in connection with the fastener web. The term "the mantle surface of the preform projections at least partially tapers from the attached end to the top surface of the terminal end in the direction of the terminal end" means that the mantle surface of the preform projections essentially continuously tapers in the direction to the terminal end over at least part of its extension. The precursor web is suited for manufacturing a fastener with reproducible properties of the pattern. The mantle surfaces of the preform projections can be formed to be of convex, particularly lenticular or cup-type, essentially straight and/or concave shape, and it is further possible to realize preform projections having different shapes and/or distribution in each pattern.

In the drawings, the invention is illustrated in greater detail by means of exemplary embodiments.

Figure 1A:
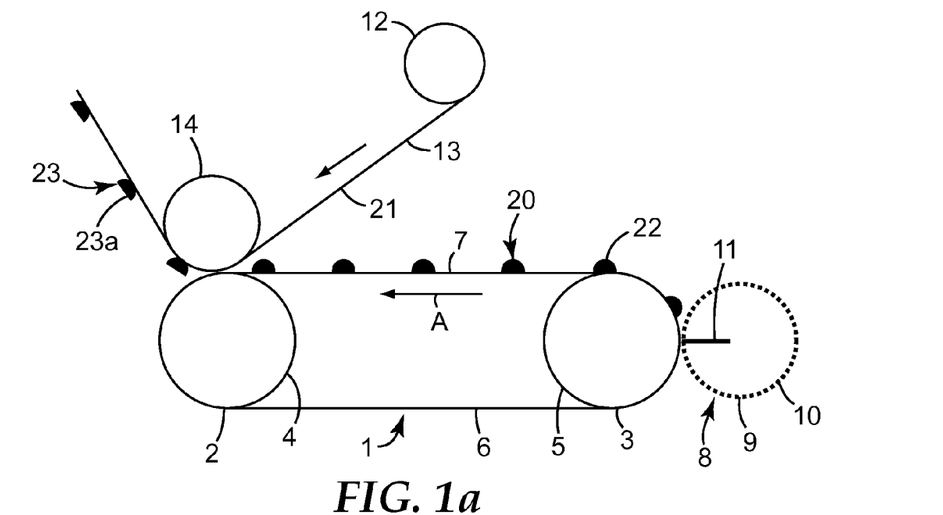
FIGS. 1a, 1b are schematic side views of a first embodiment of the apparatus for manufacturing a fastener of the invention.

In FIG. 1a, an apparatus 1 for manufacturing male fasteners is shown. The apparatus 1 has two rolls 2, 3 disposed at a distance, the rotational axes extend perpendicularly to the drawing plane and parallel relative to each other. The rolls 2, 3 are cylindrical having mantle surfaces 4, 5 about which a flexible belt 6 is tensioned forming a closed loop that extends horizontally between the two rolls 2, 3. The outside of the belt 6 offers a contact release surface 7.

Beneath the right roll 3 and separated by the belt 6, a rotary screen device 8 is disposed comprising a cylindrical rotary screen 9, which is rotatable about a rotational axis extending perpendicularly to the drawing plane. The rotary screen 9 has numerous through holes 10 distributed about the mantle surface of the rotary screen 9 in a specific pattern. A squeegee 11 is disposed inside the rotary screen 9 in a fixed position with one edge lying closely to the inner surface of the rotary screen 9.

Above the belt 6, a further roll 12 is disposed having a rotational axis extending parallel to the rotational axes of the rolls 2, 3. Onto the roll 12, a carrier web 13 is wound. A part of this carrier web 13 is already unwound and extends to a further roll 14, which is freely rotatable and disposed above the left roll 2 having a rotational axis extending parallel to the rotational axis of the roll 12. Roll 12 and roll 2 form a nip between themselves, through which the carrier web 13 passes partly wrapping the mantle surface of roll 14. Thereafter, the carrier web 13 leaves the mantle surface and is guided to another roll (not shown), onto which the carrier web 13 is wound again.

For manufacturing of a male fastener, at least one of the rolls 2, 3 is driven by an electric motor so that the belt 6 is moving in the direction of arrow A. The rotary screen 9 is driven by an electric motor, too and the circumferential velocity is equal to the circumferential velocity of roll 3, but in clockwise direction. Molten polymer material is fed in a conventional manner into the interior space of the rotary screen 9 and in the region where the squeegee 11 contacts the inside of the rotary screen 9. Thereby, the molten polymer material is squeezed through the holes 10 of the rotary screen 9 and then deposited onto the contact release surface 7 forming discrete drop-like preform projections 20 with a convex mantle surface which are displayed in an enlarged scale.

The preform projections 20 are distributed on the contact release surface 7 in accordance with the pattern of the holes 10 in the rotary screen 9. This pattern repeats with every revolution of the rotary screen 9 exactly. However, it is also possible to provide more than one identical patterns of holes 10 in circumferential direction so that an according number of repetitions of the pattern will be achieved by one revolution of the rotary screen 9.

Simultaneously, the carrier web 13 is drawn from the roll 12 with a velocity equal to the velocity of the belt 6. During the transport, the preform projections 20 solidify next to the contact release surface 7 thereby adhering onto the surface sufficiently so that they do not move relative to the belt 6. The velocity of the belt 6 and the ambient condition are controlled so that the terminal ends 22 of the preform projections 20 are maintained in an at least semi-molten state when they reach the nip between the roll 2 and the roll 14. The distance between the carrier web 13 and the belt 6 in the nip is adjusted so that the front surface 21 of the carrier web 13 contacts the terminal ends 22 of the preform projections 20 and bonds them to the front surface 21. The preform projections 20 are separated from the contact release surface 7, when the carrier web 13 leaves the nip between rolls 2, 14, thereby forming discrete cup-like fastening members 23 having flat terminal ends 23a. If the contact release surface 7 is textured or microreplicated, the terminal ends 23a of the fastening members 23 have accordingly structured surfaces. Carrier web 13 and fastening members 23 form a fastener web which is wound onto a roll, and can then be cut into portions which can be used as fasteners. These fasteners can be fixed for example to disposable diapers, training pants and incontinence garments or any other hygiene or absorbent article.

Figure 1B:
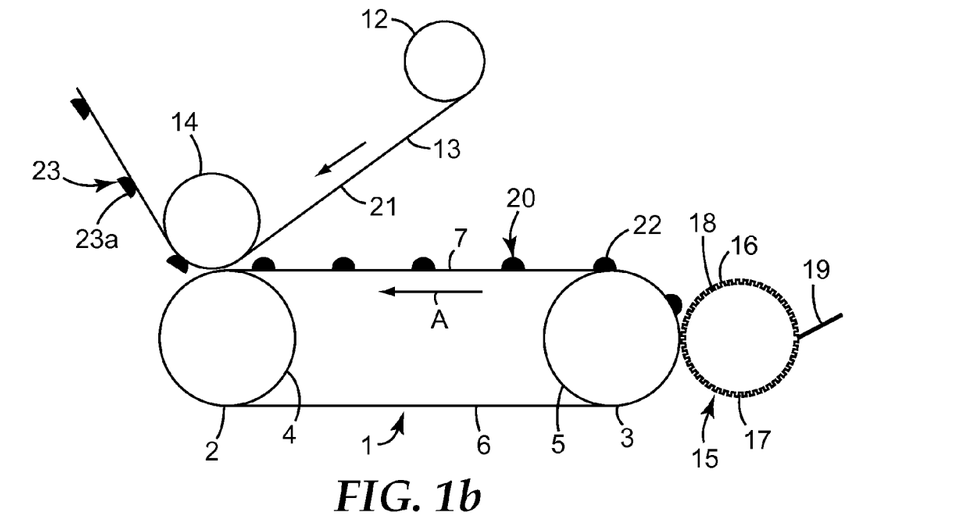

The apparatus of FIG. 1b differs from the apparatus of FIG. 1a in that a printing roll device 15 is used instead of the rotary screen device 8. The printing roll 16 comprises a mantle surface 17, which provides numerous cavities 18, which are open to the mantle surface 17. The cavities 18 are distributed about the mantle surface 17 in a specific pattern. A doctor blade 19 is disposed outside the printing roll 16, one edge of which is contacting the mantle surface 17. In the apparatus of FIG. 1b, the molten polymer material is fed onto the mantle surface 17 of the printing roll 16 in a conventional manner and pressed into the cavities 18 by the doctor blade 19. Due to the contact between the mantle surface 17 of the printing roll 16 and the contact release surface 7 of the belt 6, the polymer material adheres to the contact release surface 7 and is extracted out of the cavities 18, thereby forming preform projections 20 having a base in accordance with the shape of the opening of the cavities 18.

The further embodiments of the apparatus for manufacturing a fastener of the invention are similar in some aspects so that in the following embodiments, only the differences to the apparatus shown in the foregoing figure(s) are described and the reference numbers are used also for the further embodiments as far as they mark the same devices as described in connection with a foregoing figure.

Figure 2:
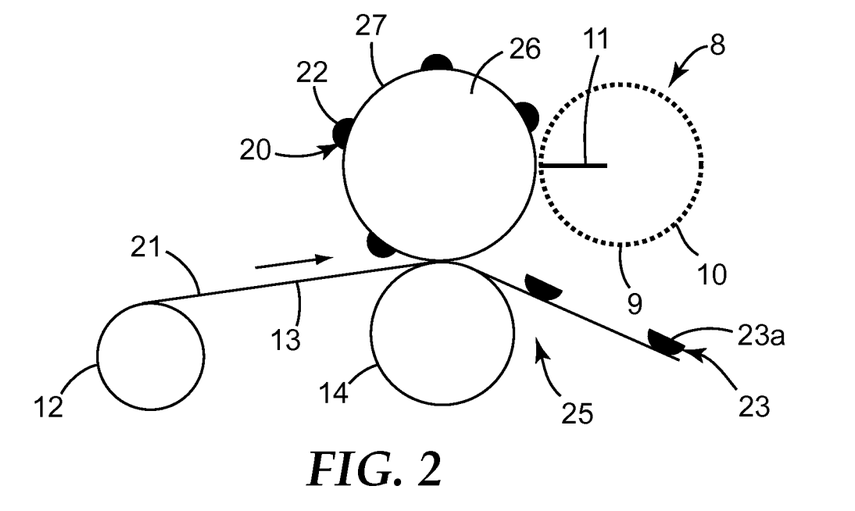
FIG. 2 is a schematic side view of a second embodiment of the apparatus for manufacturing a fastener of the invention.

In FIG. 2, an apparatus 25 for manufacturing male fasteners is shown. The rolls 2, 3 and the belt 6 of the apparatus 1 are replaced by a cylindrical roll 26 having a rotational axis extending perpendicular to the drawing plane. The mantle surface of the roll 26 forms a contact release surface 27 with the rotary screen 9 of the rotary screen device 8 being located nearby. The roll 14 is disposed below the roll 26 in a distance so that a nip is formed through which the carrier web 13 is guided. The carrier web 13 is unwound from the roll 12 and leads to another roll (not shown) where the carrier web 13 is wound again.

For the manufacturing of male fasteners, the roll 26 and the rotary screen 9 are driven in opposite directions having equal circumferential velocities. Molten polymer material is squeezed through the holes 10 of the rotary screen 9 and then deposited onto the contact release surface 27 of the roll 26 forming discrete drop-like preform projections 20 with convex mantle surfaces. Since the roll 26 is cooled, the preform projections 20 solidify next to the contact release surface 27 thereby sufficiently adhering to the surface. The speed of the roll 26 and its temperature is controlled so that the terminal ends 22 of the preform projections 20 are maintained in an at least semi-molten state, when they reach the nip between roll 26 and roll 14. The carrier web 13 is drawn from the roll 12 with a velocity equal to the circumferential velocity of the contact release surface 27 of the roll 26. The distance between the carrier web 13 and the roll 26 in the nip is adjusted so that the front surface 21 of the carrier web 13 contacts the terminal ends 22 of the preform projections 20 and separates them from the contact release surface 27, when the carrier web 13 leaves the nip, thereby forming discrete cup-like fastening members 23 having flat terminal ends 23a.

Figure 3:
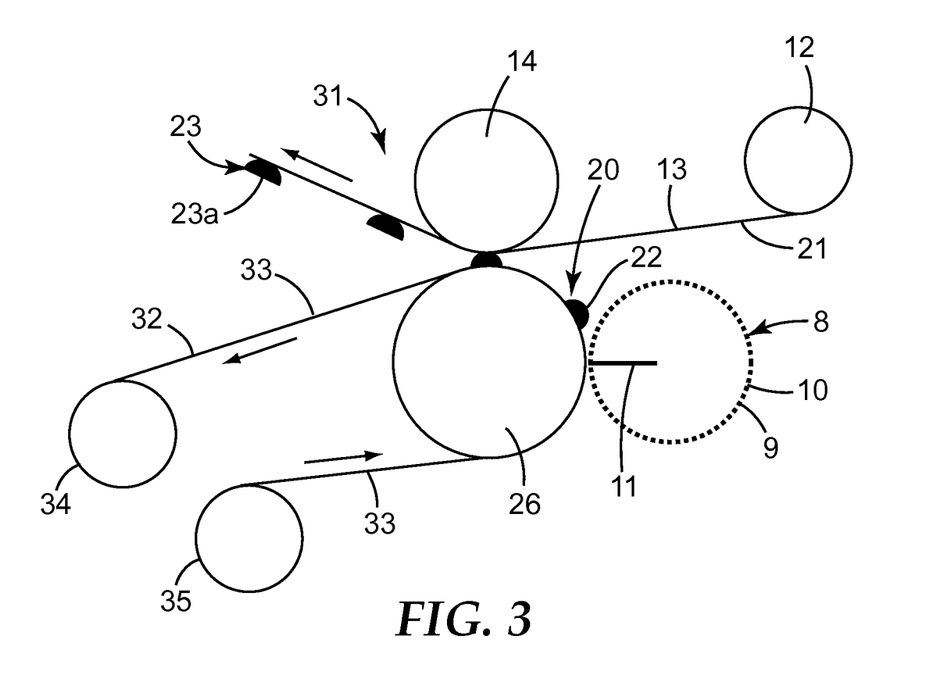
FIG. 3 is a schematic side view of a third embodiment of the apparatus for manufacturing a fastener of the invention.

In FIG. 3, a third embodiment of an apparatus 31 for manufacturing male fasteners is shown. It differs from the apparatus 25 depicted in FIG. 2 so that the roll 14 is disposed above the roll 26 and that a contact release surface 32 is not provided by the mantle surface of the roll 26 but by a substrate web 33 which can be made out of a polymeric material. The substrate web 33 is wound partly onto a roll 35, then wrapped about the mantle surface of the roll 26 and wound partly onto a roll 34.

For the manufacturing of male fasteners, the roll 26 and the rotary screen 9 are driven and the carrier web 13 is drawn from the roll 12 in the same manner as described in connection with the apparatus 25 shown in FIG. 2. Due to the friction between the substrate web 33 and the roll 26, the substrate web 33 is unwound from the roll 35, while polymer material is squeezed through the holes 10 of the rotary screen 9 and then deposited onto the contact release surface 32 of the substrate web 33 in accordance with the pattern of the holes 10 in the rotary screen 9. After having left the nip between the roll 14 and the roll 26, the substrate web 33 is wound onto the roll 34. Also in this case, the speed of the roll 26 and its temperature is controlled so that the terminal ends 22 of the preform projections 20 are maintained in an at least semi-molten state when they reach the nip between roll 26 and roll 14. The distance between the carrier web 13 and the roll 26 in the nip is adjusted so that the front surface 21 of the carrier web 13 when unwound from the roll 12, contacts the terminal ends 22 of the preform projections 20. The preform projections 20 are separated from the contact release surface 32 of the substrate web 33 when the carrier web 13 leaves the nip, thereby forming discrete cup-like fastening members 23 having flat terminal ends 23a.

Figure 4:
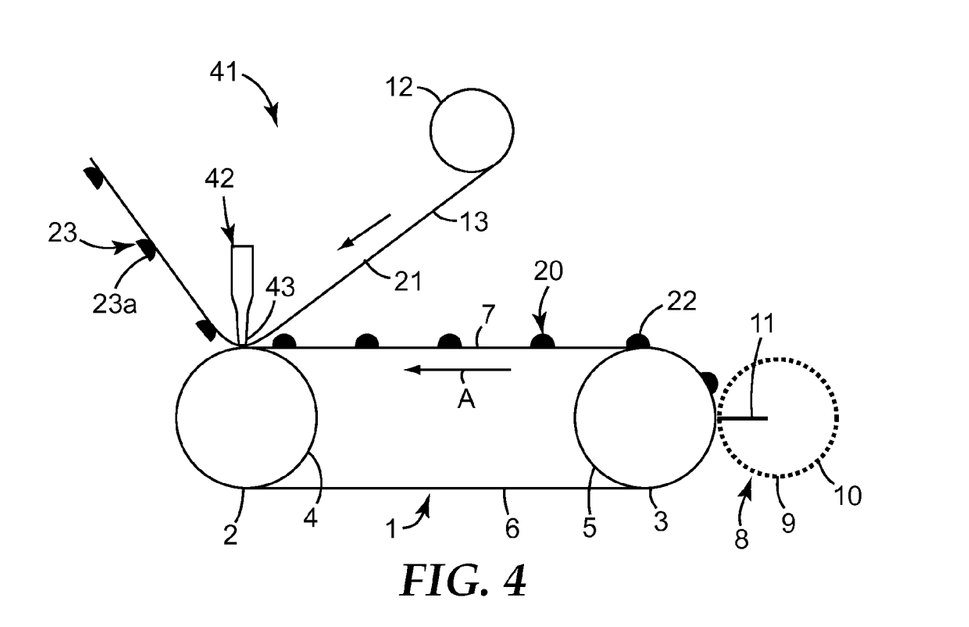
FIG. 4 is a schematic side view of a fourth embodiment of the apparatus for manufacturing a fastener of the invention.

In FIG. 4, a further apparatus 41 for manufacturing male fasteners is shown. This apparatus 41 is similar to the apparatus 1 shown in FIG. 1. Instead of the roll 14, a sonic welding unit 42 is disposed above the roll 2. The carrier web 13 is passed about the head 43 of the sonic welding unit 42 being in contact therewith.

For the manufacturing of male fasteners, the belt 6 is driven as described in connection with the apparatus 1 shown in FIG. 1, and the molten polymer material is deposited onto the contact release surface 7 of the belt 6 by the rotary screen device 8 forming preform projections 20. However, in this case the velocity of the belt 6 is controlled and the belt 6 is cooled so that all the preform projections 20 solidify completely during their transport from the rotary screen device 8 to the sonic welding unit 42. The distance between the carrier web 13 and the belt 6 in the region of the sonic welding unit 42 is adjusted so that the front surface 21 of the carrier web 13 contacts the terminals ends 22 of the preform projections 20. Due to the influence of the sonic welding unit 42, the terminal ends 22 of the preform projections 20 and also the carrier web 13 are heated to a temperature where the terminal ends 22 are re-melted. Thereby, bonding of the preform projections 20 to the front surface 21 of the carrier web 13 is achieved so that the preform projections 20 are separated from the contact release surface 7 of the belt 6 when the carrier web 13 is drawn from the roll 12 and leaves the nip between the sonic welding unit 42 and roll 2, thereby forming discrete cup-like fastening members 23 having flat terminal ends 23a.

Figure 5:
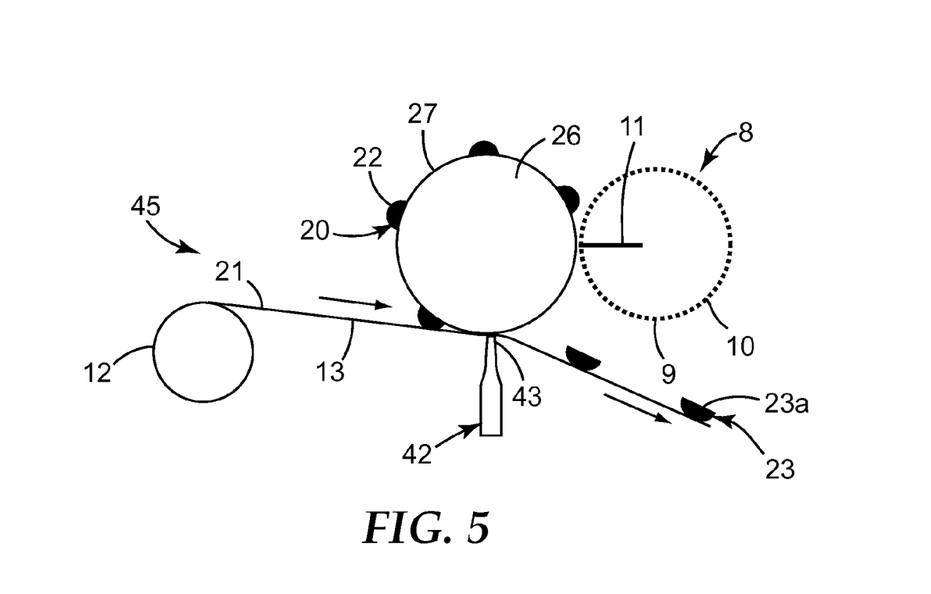
FIG. 5 is a schematic side view of a fifth embodiment of the apparatus for manufacturing a fastener of the invention.

In FIG. 5, a further apparatus 45 for manufacturing male fasteners is shown. The apparatus 45 is similar to the apparatus shown in FIG. 2. As in FIG. 4, the roll 14 in FIG. 1 is replaced with the sonic welding unit 42 as shown in FIG. 4 having a head 43 about which the carrier web 13 is guided in contact with the head 43.

For the manufacturing of male fasteners, the roll 26 and the rotary screen 9 are driven as described in connection with the apparatus 25. Molten polymer material is squeezed through the holes 10 of the rotary screen 9 and then deposited onto the contact release surface 27 of the roll 26 forming drop like preform projections 20. The roll 26 is cooled so that the preform projections 20 solidify completely before reaching the carrier web 13. The sonic welding unit 42 heats the carrier web 13 and the preform projections 20 passing through the nip between the roll 26 and the head 43 of the sonic welding unit 42, to a temperature at which the preform projections 20 and also the carrier web 13 at the spots of contact with the preform projections 20 melt so that they adhere to the front surface 21 of the carrier web 13. The perform projections 20 separate from the contact release surface 27 when the carrier web 13 leaves the nip, thereby forming discrete cup-like fastening members 23 having flat terminal ends 23a.

Figure 6:
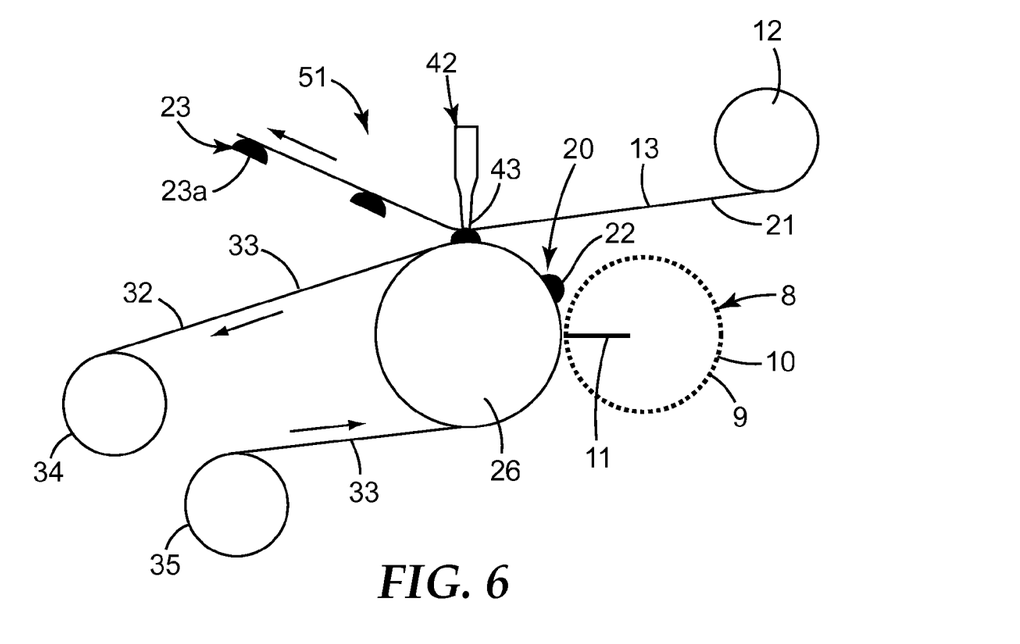
FIG. 6 is a schematic side view of a sixth embodiment of the apparatus for manufacturing a fastener of the invention.

In FIG. 6, a further apparatus 51 for manufacturing male fasteners is shown. This apparatus 51 is similar to the apparatus 31 shown in FIG. 3. However, the roll 14 is replaced by the sonic welding unit 42 of the apparatus 41 shown in FIG. 4. The carrier web 13 is guided so that it passes about the head 43 of the sonic welding unit 42 in contact therewith.

When manufacturing male fasteners, the preform projections 20 deposited by the rotary screen device 8 onto the contact release surface 32 of the substrate web 33 are transported by rotating the roll 26 counter-clockwise and moving the substrate web 33 from the roll 35 to the roll 34. In the gap between the head 43 of the sonic welding unit 42 and the roll 26, the terminal ends 22 of the preform projections 20 are re-melted and the front surface 21 of the carrier web 13 is melted at the spots where it contacts the terminal ends 22 of the preform projections 20. The bonding between the front surface 21 of the carrier web 13 and the terminal ends 22 of the preform projections 20 is so strong that the preform projections 20 are separated from the contact release surface 32 when the carrier web 13 leaves the gap, thereby forming discrete cup-like fastening members 23 having flat terminal ends 23a.

Figure 7:
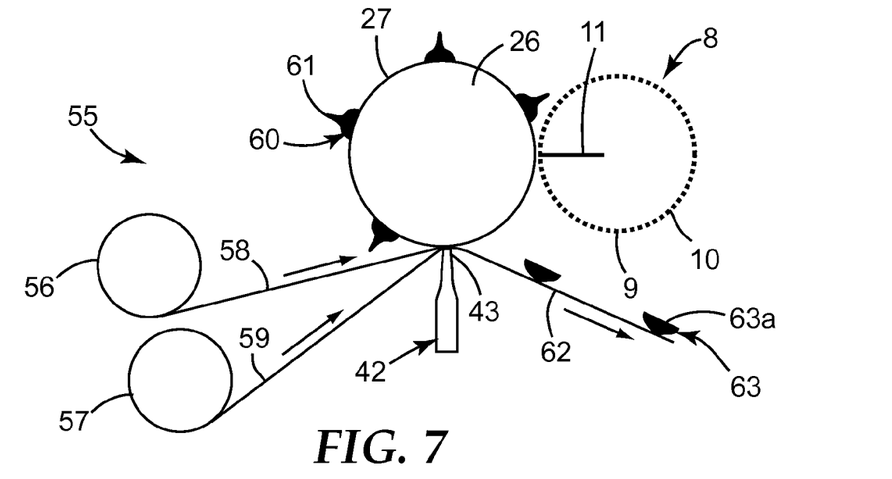
FIG. 7 is a schematic side view of a seventh embodiment of the apparatus for manufacturing a fastener of the invention.

In FIG. 7 a further embodiment of an apparatus 55 for manufacturing a male fastener is depicted. The apparatus 55 is similar to the apparatus 45 shown in FIG. 5. However, there are two rolls 56, 57 disposed one above the other, onto which webs 58, 59 are wound. The already unwound parts of these webs 58, 59 extend to the head 43 of the sonic welding unit 42 where they come into contact with each other and with the head 43 in the gap between the roll 26 and the head 43 of the sonic welding unit 42.

The holes 10 of the rotary screen device 8 are embodied and the polymer material has a viscosity so that the rotary screen 9 produces discrete preform projections 60 with concave mantle surfaces having a broad base attached to the contact release surface 27 and a small tip 61 at their terminal ends.

For the manufacturing of male fasteners, the rotary screen 9 and the roll 26 are driven in opposite directions with the rotary screen 9 clockwise. The webs 58, 59 are drawn from the rolls 56, 57. When reaching the gap between the head 43 of the sonic welding unit 42 and the roll 26, the preform projections 60 and also the webs 58, 59 are heated to a temperature at the spots where the preform projections 60 contact the web 58, thereby producing a bond so that the webs 58, 59 are connected and the preform projections 60 are separated from the contact release surface 27 of the roll 26, when the so formed carrier web 62 leaves the gap. The resulting discrete fastening members 63 thus formed have concave mantle surfaces and a flat terminal end 63a.

Figure 8:
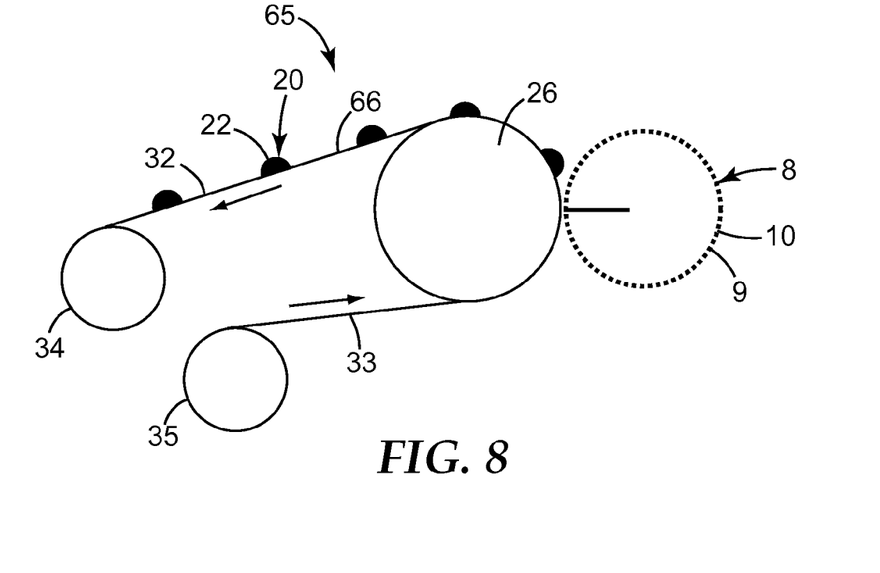
FIG. 8 is a schematic side view of an apparatus for manufacturing a precursor web of the invention.
Figure 9:
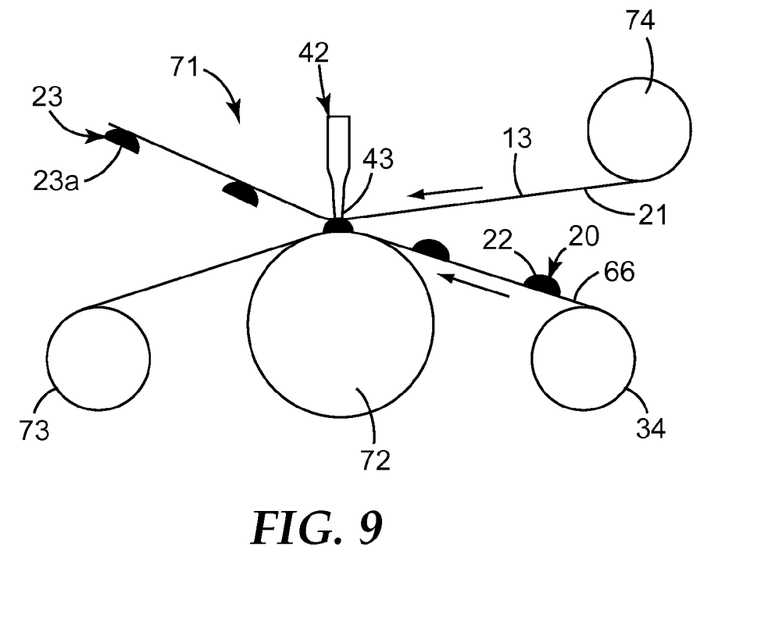
FIG. 9 is a schematic side view of an eighth embodiment of the apparatus for manufacturing a fastener with the precursor web manufactured with the apparatus shown in FIG. 8.
Figure 10A:
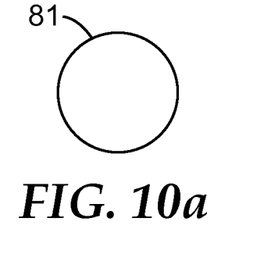
FIGS. 10a to 10g show magnified views of different cavities.
Figure 10B:
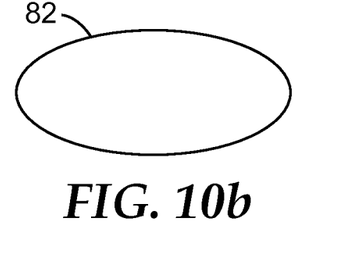
Figure 10C:
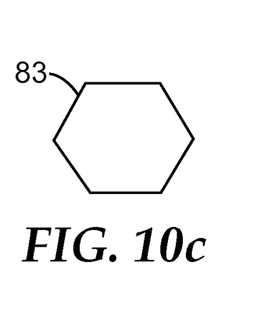
Figure 10D:
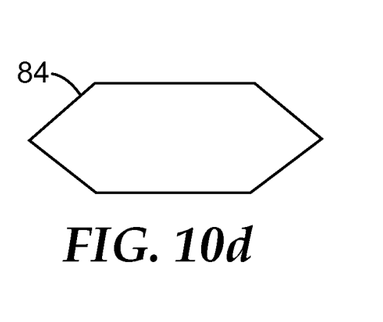
Figure 10E:
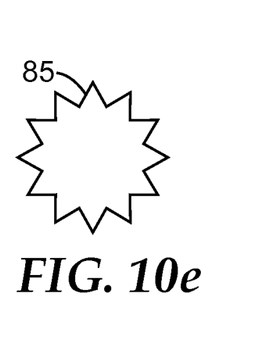
Figure 10F:
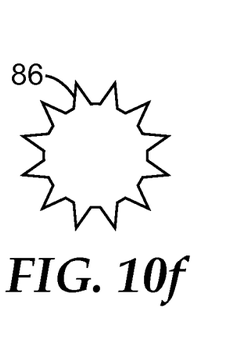
Figure 10G:
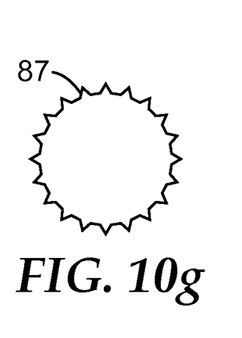

In FIG. 8, an apparatus 65 for manufacturing a precursor web is shown which is suitable for the manufacturing of male fasteners in a further apparatus as shown in FIG. 9. The basis of the apparatus 65 is the apparatus 31 shown in FIG. 3. However, the roll 12, the carrier 13 and the roll 14 are left out. Hence, the apparatus 65 consists of the roll 26, the rotary screen device 8 and the substrate web 33 wrapped about the mantle surface of the roll 26 and wound onto the rolls 34 and 35.

For the manufacturing of the precursor web, the substrate web 33 is unwound from the roll 35 and simultaneously wound onto the roll 34 by counter-clockwise rotation of roll 26. Simultaneously, the rotary screen 9 of the rotary screen device 8 rotates clockwise with the same circumferential velocity as the roll 26. Polymer material is fed to the interior of the rotary screen 9 as described above and squeezed through the holes 10 of the rotary screen 9, thereby depositing discrete preform projections 20 with terminal ends 22 forming drop-like projections with a convex mantle surface. When leaving the nip between the rotary screen 9 and the roll 26, the precursor web 66 is formed and allowed to cool sufficiently so that it can be wound onto the roll 34 without affecting the form of the preform projections 20. At the end of this process, the roll 34 with the entire precursor web 66 being wound up, can be removed from the apparatus 65 and transported to another location where it can be used for the manufacture of male fasteners.

FIG. 9 shows an apparatus 71 for manufacturing male fasteners using a precursor web 66 produced with the apparatus 65 shown in FIG. 8. The apparatus 71 comprises a roll 72. Its rotational axis extends perpendicularly to the drawing plane. On the right side of the roll 72, the roll 34 with the precursor web 66 is disposed rotatably. The already unwound part of the precursor web 66 is wrapped about the mantle surface of the roll 72 and the web itself is then wound onto a roll 73. Above the roll 34, another roll 74 is disposed having a rotational axis extending parallel to the rotational axis of the rolls 34, 72 and 73. A carrier web 13 is wound onto the roll 74, and its already unwound part is fed to the head 43 of the sonic welding unit 42 which is disposed opposite to the mantle surface of the roll 72.

For the manufacturing of male fasteners, the roll 72 is rotated counter-clockwise and the precursor web 66 is drawn from the roll 34, the preform projections 20 being on the side of the precursor web 66 opposite to the front surface 21 of the carrier web 13. The carrier web 13 is drawn from the roll 74 and passes about the head 43 of the sonic welding unit 42 forming a gap between the front surface 21 and the precursor web 66 that is small enough so that the front surface 21 contacts the terminal ends 22 of the preform projections 20. Thereby, the terminal ends 22 are re-melted and the front surface 21 of the carrier web 13 is melted at the spots where it contacts the terminal ends 22 of the preform projections 20. The bonding between the front surface 21 of the carrier web 13 and the terminal ends 22 of the preform projections 20 is so strong that the preform projections 20 are separated from the precursor web 66 when the carrier web 13 leaves the gap, thereby forming discrete cup-like fastening members 23 having flat terminal ends 23a. Thereafter, the carrier web 13 provided with the fastening members 23 can be collected preferable by coiling up onto a roll (not shown).

FIGS. 10a through 10g show different forms of cavities 81, 82, 83, 84, 85, 86, 87. The cavity 81 has a circular shape, the cavity 82 an oval shape, the cavity 83 a regular hexagonal shape with equal side length, the cavity 84 has an elongated hexagonal shape and the cavities 85, 86 and 87 exhibit star-like shapes in different configurations. FIGS. 10a through 10g show only the boarders of the cavities 81 through 87 and not the shape of the interior of the cavities 81 through 87.

Of course, through holes 10 of the rotary screen 9 shown in the FIGS. 1 through 8 can have such shapes which result in corresponding shapes of the preform projections 20 and hence of fastening memhers 23. It is possible that one rotary screen 9 or printing roll 16 may have cavities or through holes with different shapes.

Figure 11:
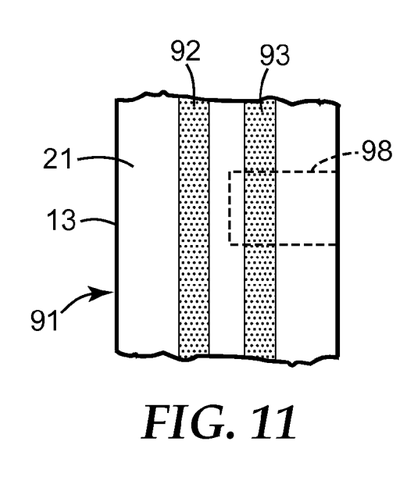
FIG. 11 is a top view of a first embodiment of a part of a fastener web.
Figure 12:
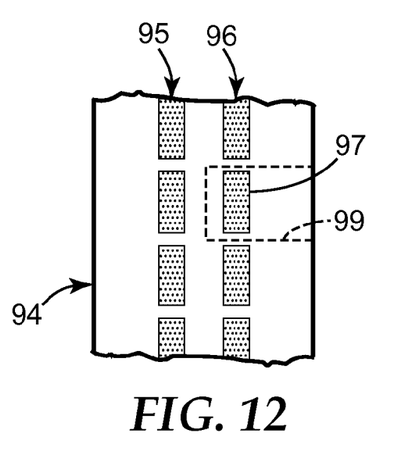
FIG. 12 is a top view of a second embodiment of a fastener web.

FIG. 11 shows a fastener web 91 comprising a carrier 13 with a front surface 21 onto which a multiplicity of discrete polymeric fastening members is bonded in two parallel extending continuous stripes 92, 93, wherein the fastening members are formed and disposed in a pattern repeating in the lengthwise direction of the stripes 92, 93. A similar fastener web 94 is shown in FIG. 12 where a multiplicity of polymeric fastening members are bonded onto the front surface 21 in intermittent stripes 95, 96 so that separated repeating patterns 97 are formed. In both FIGS. 11 and 12, the dotted lines 98, 99 indicate cuts applied to form patches suitable for the application onto a diaper. The patches have a narrow finger lift area left to the pattern 97 and a larger area right to the pattern 97 for bonding onto the diaper. The continuous stripes 92, 93 in FIG. 11 and the intermittent stripes 95, 96 in FIG. 12, respectively, comprise a multitude of individual fastening members as is indicated in FIGS. 11 and 12.

Figure 13:
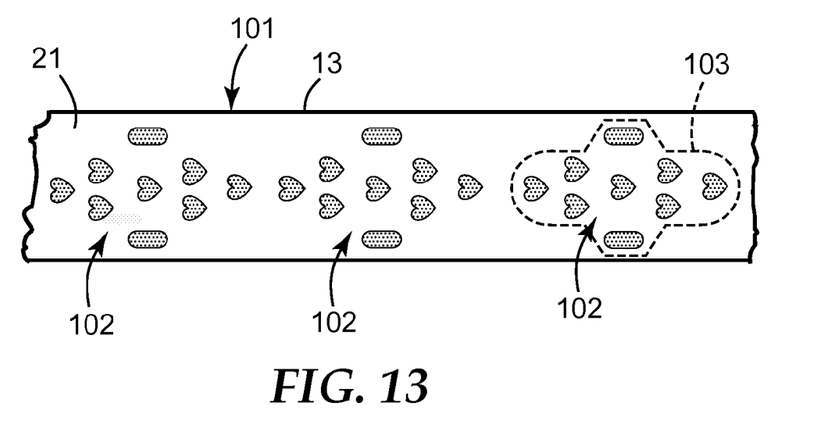
FIG. 13 is a top view of a third embodiment of a fastener web.

FIG. 13 shows a fastener web 101 comprising a carrier 13 with a front surface 21. In the oval and heart-like areas indicate the areas, a multiplicity of discrete polymeric fastening members is bonded onto the front surface 21. The repeating patterns 102 consist of seven heart-like areas and two oval areas, respectively. The heart-like areas have a lower density of fastening members and the oval areas have a higher density. A dotted line 103 indicates the cut line for the final pad. It is noteworthy that the final pad does not have fastening members in the edge areas of the pad that could cause skin irritation. The fastener web 101 comprises a multitude of individual fastening members as is indicated in FIG. 13.

The invention claimed is:
1. A method for forming a fastener having fastener members, particularly a male fastener for a hook and loop fastening system, comprising:
 providing a carrier with a front surface;
 providing a contact release surface;
 providing a deposition device having a plurality of cavities;
 providing a polymer material heated to a molten state;
 filling said molten polymer material into said cavities;

depositing said molten polymer material from said cavities onto said contact release surface having a temperature below the softening or melting temperature of said molten polymer material, thereby forming preform projections sitting on and projecting from the contact release surface to their corresponding terminal ends;

said preform projections being in contact with the contact release surface for a time sufficient to solidify next to the contact release surface;

contacting the front surface of the carrier with the terminal ends said preform projections and bonding them to the carrier;

separating the preform projections from the contact release surface; and thereby forming fastening members projecting from the front surface of the carrier.

2. The method of claim 1, wherein the terminal ends of said preform projections are still molten or semi-molten, when they contact the front surface of the carrier.

3. The method of claim 1, wherein at least some of said preform projections are in contact with the contact release surface for a time sufficient to solidify completely and then at least the terminal ends of the preform projections are re-melted to a semi-molten or molten status before and/or while contacting them with the front surface of the carrier.

4. The method of claim 3, wherein the terminal ends of the preform projections are heated in a region, where the front surface of the carrier is coming into contact with said terminal ends.

5. The method of claim 1, the front surface of the carrier is heated at least to the softening temperature of the polymer material in the region, where the preform projections come into contact with the carrier.

6. The method of claim 1, a first polymer material is used for forming the preform projections and at least the front surface of the carrier is formed out of a second material different in at least one property than the first polymer material.

7. The method of claim 1, wherein the preform projections are formed so that the fastening members bonded onto the front surface of the carrier are bonded by an attached end area and a terminal end, wherein the terminal end comprises a top surface area, wherein the attached end area is smaller than the top surface area and wherein the fastening members have a mantle surface extending between the terminal end and the attached end, wherein the mantle at least partially tapers in the direction to the attached end.

8. The method of claim 1, the terminal ends of at least some fastening members bonded onto the front surface of the carrier are deformed by re-heating them and then contacting them with a shaping surface of a shaping device.

* * * * *